United States Patent
Binmore et al.

(10) Patent No.: US 7,164,053 B2
(45) Date of Patent: Jan. 16, 2007

(54) PROCESS FOR THE PRODUCTION OF OLEFINS

(75) Inventors: Gavin Thomas Binmore, Ashford (GB); David Charles Griffiths, Claygate (GB); Brian Edward Messenger, Hook (GB); Ian Allan Beattie Reid, Southfields (GB)

(73) Assignee: Ineos Europe Limited, Middlesex (GB)

( * ) Notice: Subject to any disclaimer, the term of this patent is extended or adjusted under 35 U.S.C. 154(b) by 461 days.

(21) Appl. No.: 10/221,752

(22) PCT Filed: Feb. 22, 2001

(86) PCT No.: PCT/GB01/00759

§ 371 (c)(1),
(2), (4) Date: Oct. 4, 2002

(87) PCT Pub. No.: WO01/68571

PCT Pub. Date: Sep. 20, 2001

(65) Prior Publication Data

US 2005/0277798 A1 Dec. 15, 2005

(30) Foreign Application Priority Data

Mar. 16, 2000 (GB) .................. 0006384.2
Nov. 18, 2000 (GB) .................. 0028231.9

(51) Int. Cl.
*C07C 5/327* (2006.01)

(52) U.S. Cl. .................. 585/658; 585/660; 585/661; 585/662; 585/663

(58) Field of Classification Search ................ 585/658, 585/660–663
See application file for complete search history.

(56) References Cited

U.S. PATENT DOCUMENTS

| 3,119,883 | A |   | 1/1964  | Kluksdahl |
| 3,541,179 | A |   | 11/1970 | Okagami et al. |
| 3,751,512 | A |   | 8/1973  | Woskow et al. |
| 3,758,609 | A |   | 9/1973  | Cichowski |
| 3,810,954 | A |   | 5/1974  | Bertus |
| 3,821,324 | A |   | 6/1974  | Bertus |
| 3,856,880 | A | * | 12/1974 | Woskow et al. ............ 585/625 |
| 3,862,255 | A |   | 1/1975  | Bertus et al. |
| 3,933,933 | A |   | 1/1976  | Bertus |
| 4,010,114 | A |   | 3/1977  | Walker et al. |
| 4,164,519 | A |   | 8/1979  | Bertus |
| 4,731,351 | A |   | 3/1988  | Kimble |
| 5,028,577 | A |   | 7/1991  | Michaels et al. |

FOREIGN PATENT DOCUMENTS

| EP | 0332289 A | 9/1989 |
| WO | 9726987 A | 7/1997 |
| WO | WO 00/14035 | 3/2000 |
| WO | WO 00/14037 | 3/2000 |
| WO | WO 00/43336 | 7/2000 |
| WO | WO 00/48971 | 8/2000 |

* cited by examiner

*Primary Examiner*—Thuan Dinh Dang
(74) *Attorney, Agent, or Firm*—Nixon & Vanderhye

(57) ABSTRACT

Process for the production of an olefin from a hydrocarbon, which process comprises contacting the hydrocarbon and a molecular oxygen-containing gas with a catalyst under autothermal conditions sufficient to produce the olefin. The catalyst comprises a component (a) and a component (b), wherein component (a) is at least one metal selected from Group IIIA, Group IVA, Group VA and the transition metals and component (b) is at least one transition metal. The catalyst does not comprise either palladium or platinum.

12 Claims, 1 Drawing Sheet

Key: ● Thermocouples

Key:  • Thermocouples

PROCESS FOR THE PRODUCTION OF OLEFINS

This application is the US national phase of international application PCT/GB01/00759 filed 22 Feb. 2001, which designated the US.

The present invention relates to a process for the production of olefins.

BACKGROUND OF THE INVENTION

Olefins such as ethylene and propylene may be produced by a variety of processes, including the steam cracking of hydrocarbons or by the dehydrogenation of paraffinic feedstocks. More recently, olefins have been produced by a process known as auto-thermal cracking. In such a process, a hydrocarbon feed is mixed with an oxygen-containing gas and contacted with a catalyst which is capable of supporting combustion beyond the normal fuel rich limit of flammability. The hydrocarbon feed is partially combusted, and the heat produced is used to drive the dehydrogenation reaction.

An example of an auto-thermal cracking process is described in EP-A-0 332 289. EP-A-0 332 289 describes platinum group metals which are capable of supporting combustion beyond the fuel rich limit of flammability such as supported platinum catalysts, for example, platinum/gamma alumina spheres, and platinum/monoliths such as platinum/cordierite or mullite monoliths. WO 97/26987, describes such platinum catalysts modified with tin or copper.

More recently, auto-thermal cracking catalysts containing palladium and Group IIIA, IVA and/or transition metals have been developed. Such catalysts are described in our co-pending application GB 9930597.1.

Other transition metals such as rhodium have also been tested for their ability to catalyse auto-thermal cracking reactions. However, as described in The Journal of Physical Chemistry (Vol 97, No 45, 1993, page 11817), rhodium has a tendency to convert hydrocarbon feeds to syngas, rather than olefins (see also page 318, Natural Gas Conversion II, ® 1994 Elsevier Science BV).

Thus there remains a need for an alternative and/or an improved process for the production of olefins.

SUMMARY OF THE INVENTION

We have now found that the production of olefins by auto-thermal cracking can be catalysed by catalysts based on (a) at least one metal selected from Group IIIA, IVA, VA and the transition metals and (b) at least one transition metal and wherein the catalyst does not comprise a significant amount of platinum and/or palladium.

Advantageously, the process of the present invention achieves greater olefin selectivity and/or higher hydrocarbon conversion than prior art auto-thermal cracking processes.

Thus, accordingly, in a first aspect of the present invention there is provided a process for the production of an olefin from a hydrocarbon, which process comprises:

contacting the hydrocarbon and a molecular oxygen-containing gas with a catalyst under auto-thermal conditions sufficient to produce the olefin, wherein the catalyst comprises a component (a) and a component (b) wherein component (a) is at least one metal selected from the group consisting of Group IIIA, Group IVA, Group VA and the transition metals and component (b) is at least one transition metal wherein said catalyst (i) comprises palladium and/or platinum at a total concentration of 0 to 1 wt % inclusive or (ii) is substantially free of palladium and/or platinum added independently of the other metal components.

It should be understood that unless otherwise specified, the term "metal" covers all elements of Group IIIA, IVA, VA and the transition metal series of the Periodic Table.

For the avoidance of doubt, the elements of Group IIIA, IVA, VA and the transition metal series of the Periodic Table are as defined in Inorganic Chemistry: Principles of Structure and Reactivity, $3^{rd}$ Edition, by James E Huheey, Harper International SI edition, 1983.

For the avoidance of doubt, the metal selected from Group IIIA, Group IVA, Group VA and the transition metal of the catalyst may be present in any form, for example, as a metal, or as a metal compound (for example, a metal oxide).

Preferably, the catalyst employed in the first aspect of the present invention does not comprise either platinum or palladium.

Where platinum and/or palladium is present, the palladium and/or platinum concentration is less than 1 wt %, preferably, less than 0.8 wt %, more preferably, less than 0.5 wt %, even more preferably, less than 0.2 wt %, even more preferably, less than 0.1 wt %, most preferably, less than 0.08 wt %. In one embodiment, the palladium and/or platinum concentration is less than 0.05 wt %, for example, less than 0.01 wt % or even less than 0.001 wt %.

In a first embodiment of the present invention, the catalyst comprises as component (a) at least one metal selected from the group consisting of Group IIIA, Group IVA and Group VA and as component (b) at least one transition metal.

Suitably, the Group IIIA metal may be selected from aluminium, gallium, indium and thallium, preferably, gallium and indium.

Suitably, the Group IVA metal may be selected from germanium, tin or lead, preferably germanium and tin.

Suitably, the Group VA metal may be selected from bismuth and antimony.

Preferably, the transition metal of component (b) may be selected from the group consisting of iron, ruthenium, osmium, cobalt, rhodium, rhenium, iridium and nickel. Most preferably, the transition metal of component (b) is rhodium or cobalt, especially rhodium.

Preferably, component (a) is tin and component (b) is rhodium or cobalt, especially rhodium.

The transition metal of component (b) may nominally form between 0.01 and 5.0 wt %, preferably, between 0.01 and 2.0 wt %, and more preferably, between 0.05 and 1.0 wt % of the total weight of the catalyst. The actual loading of component (b) may be less than this nominal value because not all the metal employed during the preparation of the catalyst actually becomes incorporated in the catalyst composition. Thus, the actual loading may be between 10 and up to 100% of the nominal loading. To ensure that the desired actual loadings are achieved, the nominal metal concentrations may have to be varied accordingly. Preferably, the actual loadings are above 40%, more preferably, above 70% (eg 90 to 99%) of the nominal values. Most preferably, the actual loading of component (b) is between 0.01 and 5.0 wt %, yet more preferably, between 0.01 and 2.0 wt %, and especially, between 0.05 and 1.0 wt % of the total weight of the dry catalyst.

Suitably, where component (b) is rhodium and component (a) is tin, the nominal loading of rhodium may be in the range 0.1 to 1.0 wt % of the total weight of the dry catalyst.

Suitably, where component (b) is cobalt and component (a) is tin, the nominal loading of cobalt may be in the range 0.01 to 5 wt % of the total weight of the dry catalyst.

The atomic ratio of the transition metal of component (b) to the Group IIIA, IVA or VA metal may be 1:0.1–50.0, preferably, 1:0.1–20, more preferably, 1:0.1–12.0, even more preferably, 1:0.2–3.0, and yet more preferably, 1:0.5–1.5.

Suitably, where component (b) is rhodium and component (a) is tin, the atomic ratio of rhodium:tin is in the range 1:0.1–20.

Suitably, where component (b) is cobalt and component (a) is tin, the atomic ratio of cobalt:tin is in the range 1:0.2–3.0.

In a further embodiment of the present invention the catalyst comprises as component (a) at least one transition metal and as component (b) at least one transition metal.

Preferably, where the catalyst comprises as component (a) at least one transition metal and as component (b) at least one transition metal, the catalyst is substantially free of platinum and/or palladium added independently of the transition metal components.

Preferably, component (a) is selected from at least one transition metal from the group consisting of copper, silver and gold, most preferably copper.

Preferably, component (b) is selected from at least one transition metal from the group consisting of iron, ruthenium, osmium, cobalt, rhodium, rhenium, iridium and nickel, most preferably rhodium.

More preferably, component (a) is selected from at least one of copper, silver and gold and component (b) is rhodium.

Most preferably, component (a) is copper and component (b) is rhodium.

Where the catalyst comprises as component (b) at least one transition metal selected from the group consisting of iron, ruthenium, osmium, cobalt, rhodium, rhenium, iridium and nickel, the amount of component (b) present may nominally form 0.01 and 5.0 wt %, preferably, between 0.01 and 2.0 wt %, and more preferably, between 0.05 and 1.0 wt % of the total weight of the catalyst. The actual loading of the metal may be less than this nominal value because not all the metal employed during the preparation of the catalyst actually becomes incorporated in the catalyst composition. Thus, the actual loading may be between 10 and up to 100% of the nominal loading. To ensure that the desired actual loadings are achieved, the nominal metal concentrations may have to be varied accordingly. Preferably, the actual loadings are above 40%, more preferably, above 70% (eg 90 to 99%) of the nominal values. Most preferably, the actual loading of component (b) is between 0.01 and 5.0 wt %, preferably. between 0.01 and 2.0 wt %, and yet more preferably, between 0.05 and 1.0 wt % of the total weight of the dry catalyst.

Suitably where component (b) is rhodium and component (a) is copper, the nominal loading of rhodium may be 0.1 to 1.0 wt % based on the total weight of the catalyst.

Where component (b) is at least one transition metal selected from the group consisting of iron, ruthenium, osmium, cobalt, rhodium, rhenium, iridium and nickel and component (a) is at least one transition metal selected from the group consisting of copper, silver and gold, the atomic ratio of said component (b) to component (a) may be 1:0.1–50.0, preferably, 1:0.1–12.0, more preferably, 1:0.2–3.0, and even more preferably, 1:0.5–1.5.

Preferably, the rhodium:copper atomic ratio is 1:0.1–15, more preferably, 1:0.1–13.

In a second aspect of the present invention there is provided a process for the production of an olefin from a hydrocarbon, which process comprises:

contacting the hydrocarbon and a molecular oxygen-containing gas with a catalyst under auto-thermal conditions sufficient to produce the olefin, wherein the catalyst comprises a component (a) and a component (b) wherein component (a) is at least one metal selected from the group consisting of Group IIIA, Group IVA, Group VA and the transition metals and component (b) is rhodium.

Preferably, the catalyst employed in the second aspect of the present invention is substantially free of platinum and/or palladium added independently of the other metal components.

Where the catalyst of the second aspect of the present invention comprises palladium and/or platinum, the concentration of palladium and/or platinum is preferably less than 1 wt %, more preferably, less than 0.8 wt %, yet more preferably, less than 0.5 wt %, even more preferably, less than 0.2 wt %, even more preferably, less than 0.1 wt %, most preferably, less than 0.08 wt %. In one embodiment, the palladium and/or platinum concentration is less than 0.05 wt %, for example, less than 0.01 wt % or even less than 0.001 wt %.

In this second aspect of the present invention, component (a) is preferably a transition metal or a Group IVA metal. Suitable transition metals include copper, silver and gold, preferably, copper. Suitable Group IVA metals include germanium, tin and lead, preferably, tin.

The catalyst employed in all aspects of the present invention may be supported or unsupported. Where the catalyst is unsupported, the catalyst may be, for example, in the form of a metal gauze.

Preferably, the catalyst is a supported catalyst. The catalyst may be supported on any suitable support. Ceramic supports are generally preferred, although metal supports may also be employed.

Where ceramic supports are used, the composition of the ceramic support may be any oxide or combination of oxides that is stable at high temperatures of, for example, between 600° C. and 1200° C. Preferably, the support material has a low thermal expansion co-efficient and is resistant to phase separation at high temperatures.

Suitable ceramic supports include corderite, lithium aluminium silicate (LAS), alumina, yttria stabilised zirconia, alumina titanate, niascon, and calcium zirconyl phosphate. The support may be wash-coated, for example, with $\gamma$-$Al_2O_3$.

The structure of the support material is important, as this may affect flow patterns through the catalyst. Such flow patterns may influence the transport of reactants and products to and from the catalyst surface, thereby affecting the catalyst's activity.

Preferably, the substrate of the support has a continuous multi-channel ceramic structure, such as a foam, a regular channelled monolith or a fibrous pad. The pores of foam monolith structures tend to provide tortuous paths for reactants and products. Such supports may have 20 to 80, preferably, 30 to 50 pores per inch. Channel monoliths generally have straighter, channel-like pores. These pores are generally smaller, and there may be 80 or more pores per linear inch of catalyst.

The support may be in the form of spheres, pellets, rings or other granular shapes, or may be a thin layer or wash coat on another substrate such as a metal gauze or a fibre mat.

The catalyst employed in the process of the present invention may be prepared by any suitable method known in the art. For example, gel methods and wet-impregnation techniques may be employed. Typically, a catalyst which may be employed in the process of the present invention may be prepared by a method which comprises the steps of
(a) impregnating a support with at least one solution of at least one metal compound, complex and/or salt dissolved in a suitable solvent;
(b) drying the impregnated support obtained in step (a); and
(c) calcining the support from step (b)

In step (a) the impregnation may be carried out as a single or, preferably as multiple impregnations.

Where at least two metal solutions are used, these may be impregnated onto the support either simultaneously (co-impregnation) or sequentially.

Multiple co-impregnations or multiple sequential impregnations may be employed.

Preferably, where multiple impregnations are employed, the support is dried and then calcined between each impregnation. Preferably, the support is both dried and calcined in air.

In step (b) the impregnated support is dried preferably in air.

In step (c) the support from step (b) is calcined in any suitable medium, but preferably, in air. Calcination may be carried out a temperature within the range 150 to 1500° C., preferably, 300 to 1200° C.

The calcined support from step (c) may be reduced, for example, by heat treatment in a hydrogen atmosphere.

The catalyst may be used in the form of a fluidised or fixed bed. Preferably, a fixed bed catalyst is employed.

The process of the present invention is a process for the partial combustion of a hydrocarbon or a mixture of hydrocarbons to form olefins. The process comprises contacting a hydrocarbon or a mixture of hydrocarbons and a molecular oxygen-containing gas with a catalyst under auto-thermal conditions sufficient to produce olefins.

Any suitable molecular oxygen-containing gas may be employed for example molecular oxygen, air or molecular oxygen diluted with an unreactive gas such as nitrogen, argon, carbon dioxide or helium.

Any molar ratio of hydrocarbon to oxygen is suitable provided the desired olefin is produced in the process of the present invention. The preferred stoichiometric ratio of hydrocarbon to oxygen is 5 to 16, preferably, 5 to 13.5 times, preferably, 6 to 10 times the stoichiometric ratio of hydrocarbon to oxygen required for complete combustion of the hydrocarbon to carbon dioxide and water.

The hydrocarbon may be any hydrocarbon which can be converted to olefins preferably mono-olefins under the auto-thermal reaction conditions employed. Suitably, the hydrocarbon may be an alkane.

Preferably, the hydrocarbon is a gaseous hydrocarbon. Suitably, the gaseous hydrocarbon may be ethane, propane, butanes and mixtures thereof.

The hydrocarbon is passed over the catalyst at a gas hourly space velocity of greater than 10,000 $h^{-1}$, preferably above 20,000 $h^{-1}$ and most preferably, greater than 100,000 $h^{-1}$. It will be understood, however, that the optimum gas hourly space velocity will depend upon the pressure and nature of the feed composition.

Advantageously, the hydrocarbon may be pre-heated. The temperature to which the hydrocarbon, oxygen-containing gas and (optionally) hydrogen mixture may be preheated, however, is limited by the autoignition temperature of the feed.

Preferably, hydrogen is co-fed with the hydrocarbon and molecular oxygen-containing gas into the reaction zone. The molar ratio of hydrogen to oxygen can vary over any operable range provided that the desired olefin product is produced. Suitably, the molar ratio of hydrogen to oxygen is in the range 0.2 to 4, preferably, in the range 0.5 to 3.

In the presence of the catalyst, hydrogen combusts preferentially relative to the hydrocarbon, thereby increasing the olefin selectivity of the overall process.

In addition, the feed may comprise a diluent such as nitrogen, carbon monoxide and steam.

The partial combustion reaction may be suitably carried out at a catalyst exit temperature of between 600° C. and 1200° C., preferably between 850° C. and 1050° C. and most preferably, between 900° C. and 1000° C.

The process of the present invention may be carried out at atmospheric or super atmospheric pressure. Suitably, the pressure may be within the range 0 to 2 bara, preferably, 1.5 to 2 bara, for example, 1.8 bara. Pressures of, for example, 2 to 50 bara, may also be suitable.

Where the cracking reaction is carried out at super atmospheric pressure the reaction products may be quenched, for example, with water, as they emerge from the reaction chamber to avoid further reactions taking place.

Any coke produced in the process of the present invention may be removed by mechanical means or by decoking. Suitable decoking methods are described in EP 0 709 446.

BRIEF DESCRIPTION OF THE DRAWING

The present invention will now be illustrated, by way of example, with reference to FIG. 1 and the following Examples.

DETAILED DESCRIPTION OF THE PREFERRED EMBODIMENT

Figure 1:
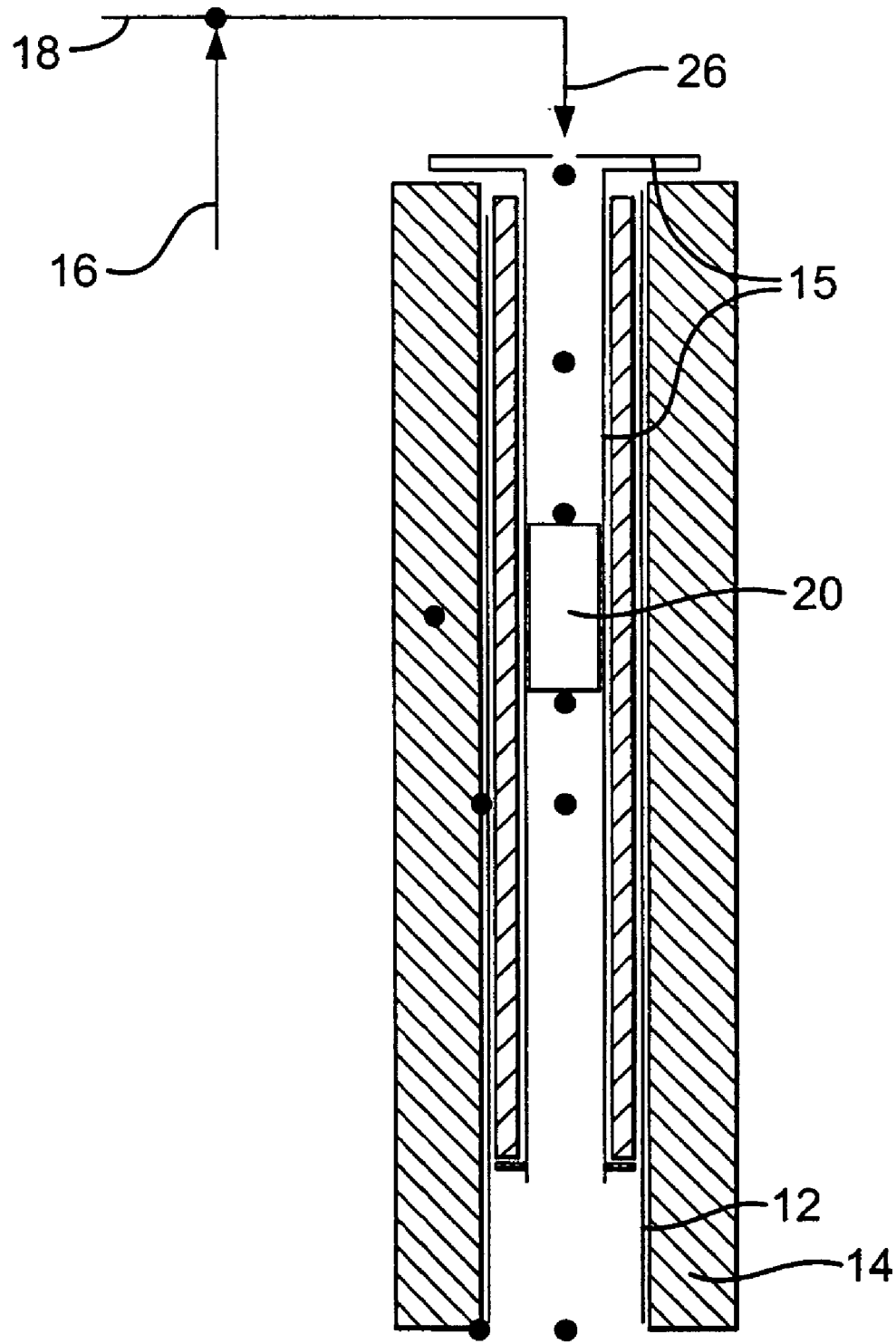
FIG. 1 is a schematic diagram of an apparatus suitable for carrying out the process of the present invention and, in particular, the dehydrogenation of ethane to ethylene.

The apparatus comprises a reactor (12) surrounded by a furnace (14). The reactor (12) is formed of metal, and lined with quartz (15).

The reactor (12) is coupled to an oxygen supply (16) and a hydrocarbon feed supply (18). The hydrocarbon feed comprises ethane, and small amounts of hydrogen and nitrogen. A catalyst (20) is located within the reactor (12). The catalyst (20) is placed between a pair of LAS heat shields (not shown).

The furnace (14) is set to minimise heat losses, and the reactants are introduced into the reactor (12) via line (26). As the reactants contact the catalyst (20), some of the ethane in the hydrocarbon feed combusts to produce water and carbon oxides. The hydrogen co-feed also combusts to produce water. Both of these combustion reactions are exothermic, and the heat produced is used to drive the dehydrogenation of ethane to ethylene.

EXAMPLES

All Ceramic Foam Supports used in the Following Examples and Experiments were Supplied by Vesuvius Hi-Tech Ceramics

Example 1

Preparation of Rh/Sn Catalyst (372-D)

The catalyst was prepared by multiple impregnation of a 30 ppi lithium aluminium silicate support having a high purity alumina (HPA) wash-coat. The support, a cylinder of diameter 15 mm, length 30 mm, was pre-treated by calcination to 1200° C. in air for 6 hours. After cooling, the support was impregnated with (a) a rhodium solution (4.85 mg/g support of rhodium (II) chloride dihydrate in 1 ml/g support of water and then (b) impregnated with a tin solution (64 mg/g support of tin (II) chloride in 1 ml/g support of water). The impregnations (a) and (b) were repeated twice further. Between each impregnation, the impregnated support was dried in air at 120° C., and then calcined in air at 450° C. for approximately 30 minutes. After the final impregnation, the resulting supported catalyst was calcined in air at 600° C. for 6 hours, and then reduced in an atmosphere of hydrogen (0.1 nl/min) and nitrogen (1.5 nl/min) for 1 hour (at 750° C.).

The (nominal) loadings of the catalyst were 0.2 wt % rhodium and 4.0 wt % tin.

Experiment A—1 wt % Pt (337)

A catalyst having a nominal loading of 1 wt % platinum was prepared by impregnating a 30 ppi lithium aluminium silicate support having an HPA wash-coat in an aqueous solution of tetraammine platinum dichloride monohydrate (18 mg/g support of tetraammine platinum dichloride monohydrate in 2 ml/g support of water). Six separate impregnations of the support were carried out. Between each impregnation the impregnated support was dried in air at 120° C., and then calcined in air at 400° C. for approximately 30 minutes. After the final impregnation, the resulting supported catalyst was calcined in air at 1200° C. for 6 hours.

Experiment B—1 wt % Rh (378B)

A catalyst having a nominal loading of 1 wt % rhodium was prepared by impregnating a lithium aluminium silicate support in a rhodium solution (24.3 mg/g support of rhodium (III) chloride dihydrate in 1 ml/g support of water ). Three separate impregnations were carried out. Between each impregnation, the support was dried in air at 120° C., and then calcined in air at 450° C. for approximately 30 minutes. After the final impregnation, the resulting supported catalyst was calcined in air at 600° C. for 6 hours.

Example 2

Oxidative dehydrogenation of ethane was carried out using each of the catalysts from Example 1, Experiment A and Experiment B. The reaction was carried out using the apparatus of FIG. 1 at atmospheric pressure. The feed was pre-heated to 200° C. The reaction conditions employed are given in Table 1. Table 1 also shows the activity and selectivity to ethylene exhibited by the catalysts.

TABLE 1

|  | Example 1 (rhodium/tin) | Experiment A (platinum only) | Experiment B (rhodium only) |
| --- | --- | --- | --- |
| GHSV @ stp/h | 194384 | 199870 | 194611 |
| ethane flow (g/min) | 9.33 | 9.56 | 8.89 |
| hydrogen flow (g/min) | 0.51 | 0.53 | 0.53 |
| oxygen flow (g/min) | 4.10 | 4.21 | 4.27 |
| nitrogen flow (g/min) | 2.01 | 2.10 | 1.59 |
| ethane conversion (%) | 73.68 | 74.91 | 72.75 |
| selectivity (g ethylene per 100 g ethane converted) | 71.22 | 69.61 | 65.28 |

From Table 1 it can be seen that the catalyst of Example 1 has greater activity and/or selectivity to ethylene than the catalysts of Experiments A and B.

Example 3

Preparation of Rhodium (0.2 wt %)/Copper (1.5 wt %) on 99.5% Alumina (396D)

3 cylindrical alumina (99%) foam blocks (30 ppi, 28 mm diameter, 30 mm deep) were impregnated with (a) an aqueous solution of rhodium(III) chloride (5.6 mg/g support of rhodium (III) chloride in 1 ml/g support of water) and then impregnated with (b) an aqueous solution of copper(II) nitrate (5.8 mg/g support of copper (II) nitrate in 1 ml/g support of water). The impregnations (a) and (b) were repeated twice further. Between each impregnation, the impregnated foam blocks were dried in air at 120° C., and then calcined in air at 450° C. for approximately 30 minutes. After the final impregnation, the blocks were calcined in air at 600° C. for 1 hour. The impregnated blocks had a nominal loading of 0.2 wt % rhodium and 1.5 wt % copper.

Example 4

The catalyst of Example 3 was loaded into the reactor of FIG. 1 and heat-treated with hydrogen at 750° C. for 1 hour. The treated catalyst was then used in the oxidative dehydrogenation of ethane under different reaction conditions ((I) and (II)) as given in Table 2. The reactor was operated at atmospheric pressure and the feed was preheated to 200° C. The results are given in Table 3.

TABLE 2

|  | Reaction Conditions (I) | Reaction Conditions (II) |
| --- | --- | --- |
| GHSV @ stp/h | 119969 | 119946 |
| Ethane flow (g/min) | 18.94 | 14.05 |
| hydrogen flow (g/min) | 1.14 | 0.91 |
| Oxygen flow (g/min) | 9.09 | 7.31 |
| Nitrogen flow (g/min) | 4.60 | 13.83 |

TABLE 3

|  | Catalyst of Example 3 under Reaction Conditions (I) | Catalyst of Example 3 under Reaction Conditions (II) |
| --- | --- | --- |
| ethane conversion (%) | 76.23 | 76.85 |
| selectivity (g ethylene per 100 g ethane converted) | 72.91 | 72.17 |

Example 5

Preparation of Rh/Sn Catalyst (377-A)

The catalyst was prepared by multiple impregnation of a 30 ppi alumina (99%) support having a high purity alumina (HPA) wash-coat. The support, a cylinder of diameter 15 mm, length 30 mm, was pre-treated by calcination to 1200° C. in air for 6 hours. After cooling, the support was impregnated with (a) a rhodium solution (23.5 mg/g support of rhodium (III) chloride dihydrate in 1 ml/g support of water), and then impregnated with (b) a tin solution (67.6 mg/g support of tin (II) chloride in 1 ml/g support of water 1 ml/g support). The impregnations (a) and (b) were repeated twice further. Between each impregnation, the impregnated support was dried in air at 120° C., and then calcined in air at 450° C. for approximately 30 minutes. After the final impregnation, the resulting supported catalyst was calcined in air at 600° C. for 6 hours. The (nominal) loadings of the catalyst were 1 wt % rhodium and 4.0 wt % tin

Example 6

Preparation of Rh/Sn Catalyst (378-C)

The catalyst was prepared by multiple impregnation of a 30 ppi lithium aluminium silicate foam support. The support, a cylinder of diameter 15 mm, length 30 mm, was impregnated with (a) a rhodium solution (4.73 mg/g support of rhodium (III) chloride dihydrate in 1 ml/g support of water), and then impregnated with (b) a tin solution (3.84 mg/g support of tin (II) chloride in 1 ml/g support of water). The impregnations (a) and (b) were repeated twice further. Between each impregnation, the impregnated support was dried in air at 120° C., and then calcined in air at 450° C. for approximately 30 minutes. After the final impregnation, the resulting supported catalyst was calcined in air at 600° C. for 6 hours. The (nominal) loadings of the catalyst were 0.2 wt % rhodium and 0.2 wt % tin

Example 7

Preparation of Rh/Sn Catalyst (378-D)

The catalyst was prepared by multiple impregnation of a 30 ppi lithium aluminium silicate foam support. The support, a cylinder of diameter 15 mm, length 30 mm, was impregnated with (a) a rhodium solution (23.6 mg/g support of rhodium (III) chloride dihydrate in 1 ml/g support of water), and then impregnated with (b) a tin solution (17.5 mg/g support of tin (II) chloride in 1 ml/g support of water). The impregnations (a) and (b) were repeated twice further. Between each impregnation, the impregnated support was dried in air at 120° C., and then calcined in air at 450° C. for approximately 30 minutes. After the final impregnation, the resulting supported catalyst was calcined in air at 600° C. for 6 hours. The (nominal) loadings of the catalyst were 1 wt % rhodium and 1.2 wt % tin Experiment C—Preparation of Rh Catalyst (378-A)

The catalyst was prepared by multiple impregnation of a 30 ppi lithium aluminium silicate foam support. The support, a cylinder of diameter 15 mm, length 30 mm, was impregnated with (a) a rhodium solution (4.68 mg/g support of rhodium (III) chloride dihydrate in 1 ml/g support of water). Three separate impregnations were carried out. Between each impregnation, the support was dried in air at 120° C., and then calcined in air at 450° C. for approximately 30 minutes. After the final impregnation, the resulting catalyst was calcined in air at 600° C. for 6 hours. The (nominal) loading of the catalyst was 0.2 wt % rhodium

Example 8

The catalysts of Examples 5–7, and Experiment C were loaded into the reactor of FIG. 1 and heat-treated with hydrogen at 750° C. for 1 hour. The treated catalyst was then used in the oxidative dehydrogenation of ethane. The results are given in Table 4.

TABLE 4

| | Catalyst of Example 5 Rh/Sn ATC-1 223 | Catalyst of Example 6 Rh/Sn ATC-1 225 | Catalyst of Example 7 Rh/Sn ATC-1 227 | Catalyst of Experiment C Rh only ATC-1 226 |
|---|---|---|---|---|
| GHSV @ stp/h | 194170 | 194544 | 194279 | 194519 |
| ethane flow (g/min) | 9.33 | 9.33 | 9.33 | 9.33 |
| hydrogen flow (g/min) | 0.51 | 0.51 | 0.51 | 0.51 |
| oxygen flow (g/min) | 4.10 | 4.10 | 4.10 | 4.10 |
| nitrogen flow (g/min) | 1.98 | 2.02 | 1.99 | 2.02 |
| ethane conversion (%) | 67.24 | 73.44 | 72.74 | 71.70 |
| selectivity (g ethylene per 100 g ethane converted) | 68.08 | 69.99 | 70.18 | 67.69 |

As Table 4 clearly shows, the catalysts of Examples 5–7 demonstrate greater selectivity and/or activity than the catalyst of Experiment C.

Example 9

Preparation of Rh/Cu Catalyst—390B 3 cylindrical alumina (99%) foam blocks (30 ppi, 28 mm diameter*30 mm deep) were impregnated with (a) an aqueous solution of rhodium(III) chloride (5.05 mg/g support of rhodium (III) chloride in 1 ml/g support of water) and then impregnated with (b) an aqueous solution of copper(II) nitrate (2 mg/g support of copper (II) nitrate in 1 ml/g support of water). The impregnations (a) and (b) were repeated twice further. Between each impregnation, the foam blocks were dried in air at 120° C., and then calcined in air at 450° C. for approximately 30 minutes. After the final impregnation, the blocks were calcined in air at 600° C. for 6 hours. The final nominal loadings of the catalyst were 0.2 wt % rhodium and 0.5 wt % copper.

Example 10

The catalyst of Example 9 was loaded into the reactor of FIG. 1 and heat-treated with hydrogen at 750° C. for 1 hour. The treated catalyst was then used in the oxidative dehydrogenation of ethane. The results are given in Table 5.

TABLE 5

| | Catalyst of Example 9 Rh/Cu ATC-2 472 |
|---|---|
| GHSV @ stp/h | 119697 |
| ethane flow (g/min) | 19.89 |
| hydrogen flow (g/min) | 1.09 |
| oxygen flow (g/min) | 8.75 |
| nitrogen flow (g/min) | 4.5 |
| ethane conversion (%) | 62.68 |
| selectivity (g ethylene per 100 g ethane converted) | 75.48 |

Example 11

Preparation of Co/Sn Catalyst—(384A)

3 cylindrical alumina (99%) foam blocks (30 ppi, 15 mm diameter*30 mm deep) were impregnated with (a) an aqueous solution of cobalt (II) nitrate hexahydrate (248 mg/g support of cobalt (II) nitrate hexahydrate in 1 ml/g support of water) and then impregnated with (b) an aqueous solution of tin (II) chloride (75.8 mg/g support of tin (II) chloride in 1 ml/g support of water). The impregnations (a) and (b) were repeated twice further. Between each impregnation, the foam blocks were dried in air at 120° C., and then calcined in air at 450° C. for approximately 30 minutes. After the final impregnation, the blocks were calcined in air at 600° C. for 6 hours. The final nominal loadings of the catalyst were 5 wt % cobalt and 5 wt % tin.

Experiment D—Preparation of Co Catalyst—(326)

5 cylindrical 30 ppi lithium aluminium silicate foam blocks with HPA washcoat (15 mm diameter*30 mm deep) were impregnated with an aqueous solution of cobalt (II) nitrate hexahydrate (259 mg/g support of cobalt (II) nitrate hexahydrate in 2 ml/g support of water). Six separate impregnations were carried out. Between each impregnation the foam blocks were dried in air at 120° C. and then calcined in air at 450° C. for approximately 30 minutes. After the final impregnation, the blocks were calcined in air at 1200° C. for 6 hours. The final nominal loading of the catalyst was 5 wt % cobalt.

Example 12

The catalysts of Example 11 and Experiment D were loaded into the reactor of FIG. 1 and heat-treated with hydrogen at 750° C. for 1 hour. The treated catalyst was then used in the oxidative dehydrogenation of ethane. The results are given in Table 6.

TABLE 6

| | Catalyst of Experiment D Co ATC-1 234 | Catalyst of Example 11 Co/Sn ATC-1 251 |
|---|---|---|
| GHSV @ stp/h | 194201 | 193363 |
| ethane flow (g/min) | 9.33 | 9.26 |
| hydrogen flow (g/min) | 0.51 | 0.51 |
| oxygen flow (g/min) | 4.1 | 4.08 |
| nitrogen flow (g/min) | 1.99 | 1.98 |
| ethane conversion (%) | 72.23 | 70.02 |
| selectivity (g ethylene per 100 g ethane converted) | 62.12 | 70.91 |

As can be seen from Table 6, the catalyst of Example 11 exhibits greater selectivity to ethylene than the catalyst of Experiment D.

The invention claimed is:

1. A process for the production of an olefin from a hydrocarbon, which process comprises:
    contacting the hydrocarbon and a molecular oxygen-containing gas with a supported catalyst under autothermal conditions such that the hydrocarbon feed is partially combusted, and the heat produced is used to drive a dehydrogenation reaction to produce the olefin, wherein the supported catalyst comprises a component (a) and a component (b) wherein component (a) is at least one metal selected from the group consisting of Group IIIA, Group IVA, Group VA and the transition metals and component (b) is at least one transition metal, selected from rhodium and cobalt,
    wherein if palladium and/or platinum is present, the palladium and/or platinum concentration is less than 1 wt %, and
    wherein the hydrocarbon and a molecular oxygen-containing gas are contacted with the catalyst at a gas hourly space velocity of at least 100,000 $hr^{-1}$ and the reaction is carried out at a catalyst exit temperature of between 600° C. and 1200° C.

2. A process as claimed in claim 1 wherein component (b) is rhodium.

3. A process as claimed in claim 1 wherein component (a) is tin.

4. A process as claimed in claim 1, wherein the catalyst has a nominal loading of between 0.01 wt % and 5.0 wt % of component (b) based on the total weight of dry catalyst.

5. A process as claimed in claim 1, wherein the atomic ratio of component (b) to component (a) is 1:0.1–50.0.

6. A process as claimed in claim 1 wherein the catalyst comprises as component (a) at least one transition metal selected from the group consisting of copper, silver and gold.

7. A process as claimed in claim 6, wherein component (b) is rhodium.

8. A process as claimed in claim 6 wherein component (a) is copper and component (b) is rhodium.

9. A process as claimed claim 1, wherein the stoichiometric ratio of hydrocarbon to oxygen is 5 to 16 times the stoichiometric ratio of hydrocarbon to oxygen required for complete combustion of the hydrocarbon to carbon dioxide and water.

10. A process as claimed in claim 1, wherein hydrogen is co-fed with the hydrocarbon and molecular oxygen-containing gas into the reaction zone.

11. A process as claimed in claim 1 wherein said catalyst does not comprise either palladium or platinum.

12. A process as claimed in clam 1 in which component (a) comprises at least one metal selected from the group consisting of gallium, indium, germanium, tin, bismuth and antimony.

* * * * *